US011234069B2

(12) United States Patent
Barnacka et al.

(10) Patent No.: US 11,234,069 B2
(45) Date of Patent: Jan. 25, 2022

(54) EARBUD FOR DETECTING BIOSIGNALS FROM AND PRESENTING AUDIO SIGNALS AT AN INNER EAR CANAL AND METHOD THEREFOR

(71) Applicants: Anna Barnacka, Cambridge, MA (US); Jal Mahendra Panchal, Somerville, MA (US); Martin D Ring, Ashland, MA (US); Thomas Devlin, Winchester, MA (US)

(72) Inventors: Anna Barnacka, Cambridge, MA (US); Jal Mahendra Panchal, Somerville, MA (US); Martin D Ring, Ashland, MA (US); Thomas Devlin, Winchester, MA (US)

(73) Assignee: MindMics, Inc., Cambridge, MA (US)

( * ) Notice: Subject to any disclaimer, the term of this patent is extended or adjusted under 35 U.S.C. 154(b) by 0 days.

(21) Appl. No.: 16/995,742

(22) Filed: Aug. 17, 2020

(65) Prior Publication Data

US 2021/0051389 A1 Feb. 18, 2021

Related U.S. Application Data

(60) Provisional application No. 62/887,553, filed on Aug. 15, 2019.

(51) Int. Cl.
*H04R 1/10* (2006.01)
*A61B 8/12* (2006.01)
*A61B 8/06* (2006.01)

(52) U.S. Cl.
CPC ............. *H04R 1/1041* (2013.01); *A61B 8/12* (2013.01); *H04R 1/1016* (2013.01);
(Continued)

(58) Field of Classification Search
CPC .. H04R 1/1041; H04R 1/1016; H04R 1/1075; A61B 8/12
See application file for complete search history.

(56) References Cited

U.S. PATENT DOCUMENTS 4,763,753 A 8/1988 Killion
2010/0125218 A1 5/2010 Haartsen et al.
(Continued)

FOREIGN PATENT DOCUMENTS

WO PCT/US2019/017832 8/2019
WO WO-2019160939 A2 * 8/2019 ............... A61B 8/02

*Primary Examiner* — Simon King
(74) *Attorney, Agent, or Firm* — Gillis Patent Law, LLC

(57) ABSTRACT

An earbud for detecting biosignals from and presenting audio signals at an inner ear canal and method therefor are disclosed. The earbud includes a nozzle and a housing including a body. The nozzle extends from the housing body and has a proximal end arranged for positioning within an inner ear canal of an individual. An earbud tip of the earbud attaches to the proximal end of the nozzle and is adapted to engage the inner ear canal. The earbud includes a speaker and various sensors including an infrasonic/vibration sensor. The infrasonic/vibration sensor detects the biosignals including infrasonic signals from the body of the individual in the canal, and the speaker transmits sound from an audio source into the canal via the nozzle. The earbud preferably seals the inner ear canal to block external sound while also decreasing an acoustic volume of the canal that amplifies the biosignals prior to detection.

20 Claims, 13 Drawing Sheets

(52) U.S. Cl.
CPC .............. *H04R 1/1075* (2013.01); *A61B 8/06* (2013.01); *H04R 2460/15* (2013.01)

(56) References Cited

U.S. PATENT DOCUMENTS

| | | | |
|---|---|---|---|
| 2011/0125063 A1* | 5/2011 | Shalon | A61B 5/4205 |
| | | | 600/590 |
| 2016/0066081 A1 | 3/2016 | Annunziato et al. | |
| 2016/0212530 A1 | 7/2016 | Liu et al. | |
| 2019/0028789 A1 | 1/2019 | Stockton et al. | |
| 2019/0247010 A1 | 8/2019 | Barnacka et al. | |
| 2019/0348041 A1* | 11/2019 | Cella | G06F 40/284 |

\* cited by examiner

EARBUD FOR DETECTING BIOSIGNALS FROM AND PRESENTING AUDIO SIGNALS AT AN INNER EAR CANAL AND METHOD THEREFOR

RELATED APPLICATIONS

This application claims the benefit under 35 USC 119(e) of U.S. Provisional Application No. 62/887,553 filed on Aug. 15, 2019, which is incorporated herein by reference in its entirety.

This application is related to:

U.S. application Ser. No. 16/274,873, filed on Feb. 13, 2019, entitled "INFRASOUND BIOSENSOR SYSTEM AND METHOD," now U.S. Patent Publication No. 2019/0247010A1; and International Application number PCT/US2019/017832, entitled "INFRASOUND BIOSENSOR SYSTEM AND METHOD," now International Application Publication No. WO2019/160939A2;

All of the aforementioned applications are incorporated herein by reference in their entirety.

BACKGROUND OF THE INVENTION

Headphones have historically referred to a pair of small speakers worn on or around the head of an individual. Each speaker in the pair is enclosed within a frame that houses the speaker and has a cushion that is placed against the outside of the ear. The speakers playback audible sound transmitted from an audio source that connects to the headphones.

Modern versions of the headphones include earphones and earbuds. These devices have much smaller frames or housings that include the speakers. Both of these devices are placed at the ear canal of the individual, while the earbuds are also partially inserted into the ear canal.

The audio source is a computing device that sends audio signals representing the audible sound to the earbuds. The speaker(s) in the earbuds convert the audio signals to sound waves corresponding to the audio signals. The sound waves include the audible sounds.

A computing device includes at least one or more central processing units (CPUs) and a memory. The CPUs have internal logic circuits that perform arithmetical operations and execute machine code instructions of applications ("application code") loaded into the memory. The instructions control and communicate with input and output devices (I/O) such as displays, printers and network interfaces.

The CPUs of the computing devices are typically configured as either microprocessors or microcontrollers. A microprocessor generally includes only the CPU in a physical fabricated package, or "chip." Computer designers must connect the CPUs to external memory and I/O to make the microprocessors operational. Microcontrollers, in contrast, integrate the memory and the I/O within the same chip that houses the CPU.

The CPUs of the microcontrollers and microprocessors execute application code that extends the capabilities of the computing devices. In the microcontrollers, the application code is typically pre-loaded into the memory before startup and cannot be changed or replaced during run-time. In contrast, the CPUs of the microprocessors are typically configured to work with an operating system that enables different applications to execute at different times during run-time.

The operating system enables application code of different applications to be loaded and executed at run-time. Specifically, the operating system can load the application code of different applications within the memory for execution by the CPU, and schedule the execution of the application code by the CPU. In addition, the operating system provides a set of programming interfaces of the CPU to the applications, known as application programming interfaces (APIs). The APIs allow the applications to access features of the CPU while also protecting the CPU. For this reason, the operating system is said to execute "on top of" the CPU.

SUMMARY OF THE INVENTION

Biosignals are signals in living beings such as individuals that can be detected, observed and/or measured. Examples of biosignals from individuals include acoustic signals, pressure signals, thermal signals and electrical signals, to name a few. The acoustic signals are created as a result of breathing and physical/mechanical operations within the individual's body. These operations include blood flow throughout the cardiovascular system, and opening and closing of valves within the heart and the blood vessels, in examples. These acoustic signals can be in either the infrasonic range (infrasonic signals) or in the audible range (audible signals) or both. The pressure signals are created by pressure or tension within the body. The thermal signals are created in response to physical and biochemical processes within the body. The electrical signals are associated with changes in electrical current over time, across a specialized tissue, organ, or cell system such as the nervous system.

Existing medical diagnostics systems for monitoring physiological functions of individuals present various levels of inconvenience and discomfort. Typically, such systems require that the individual at least attend a clinical setting/doctor's office in person. Some diagnostic systems are non-invasive, but require either attachment and placement of multiple electrodes, or placement of other sensing devices on the individual's skin. This is time-intensive and requires a trained technician or medical professional to properly set up, which increases complexity and cost. Other monitoring and diagnostic processes, such as Swan-Ganz pulmonary artery catheterization, are invasive and have a risk of adverse health effects, such as vascular or cardiac perforation, bleeding, infection and even death in some rare instances.

Infrasonic biosignals from the body of an individual can be transmitted within the human ear. The details of this transmission within the various components of the ear is complex, however. This is because the vibrations are created by different systems in the human body and can be transmitted through bones, fat, muscles, skin etc., and then into the ear. At the ear, these vibrations can become airborne, in the form of acoustic and infrasonic signals. The infrasonic signals, in particular, are transmitted at low amplitudes out of the body of the individual via the inner ear canal. These infrasonic signals carry information associated with physiological processes in the body including cardiovascular activity.

It would be advantageous to provide an earbud that can playback audio from an audio source into the inner ear canal, and can also passively detect biosignals including infrasonic signals from the individual's body via the inner ear canal. The proposed earbud can form part of a health monitoring system that can monitor physiological activity within the body of the individual, including cardiovascular activity. The detected biosignals can then be analyzed by the monitoring system to assess the health of the individual.

Unlike the existing medical diagnostics systems, the monitoring system does not require the individual to attend a clinical setting. The monitoring system easily integrates into individuals' lifestyles and does not require an extra device such as a skin-worn patch to collect the biosignals. The proposed earbud can also provide feedback to the individual in response to the monitoring via its audio playback capability, and playback music and other audible sounds as existing earbuds do.

In general, according to one aspect, the invention features an earbud including a nozzle, a housing including a body and an earbud tip. The nozzle extends from the housing body and has a proximal end arranged for positioning within an inner ear canal of an individual. The earbud tip attaches to the proximal end of the nozzle and is adapted to engage the inner ear canal. The earbud tip suspends the nozzle within the inner ear canal when engaged. The earbud also includes a speaker and an infrasonic/vibration sensor. The infrasound/vibration sensor detects biosignals including infrasonic signals from a body of the individual in the inner ear canal. The speaker reproduces sound from an audio source and transmits the sound into the inner ear canal via the nozzle.

Preferably, a face of the earbud tip forms an acoustic seal with a wall of the inner ear canal when the earbud tip is engaged. This acoustically isolates the inner ear canal from sounds external to the body of the individual. The earbud might also include a pressure sensor located within the nozzle that the earbud uses to monitor the acoustic seal. Alternatively, the earbud can use the infrasound/vibration sensor to monitor the acoustic seal. The acoustic seal increases body-generated pressure within the inner ear canal, which increases an amplitude of the biosignals in the inner ear canal.

Typically, the infrasonic/vibration sensor is included in the nozzle near the proximal end of the nozzle.

In one implementation, the nozzle includes a port located between a top surface of the infrasound/vibration sensor and an inside wall of the nozzle. In this way, the transmitted sound from the speaker propagates through the nozzle and into the inner ear canal via the port. The port has an acoustic impedance that effectively prevents the biosignals from entering the nozzle. Here, the speaker is an acoustically compliant speaker that has an effective acoustic volume that is equal to or greater than an acoustic volume of the inner ear canal.

The pressure sensor can monitor the acoustic seal or provide static pressure as a baseline for the biosignals detected by the infrasound/vibration sensor. Alternatively, the acoustic seal could be monitored using the acoustic/vibration sensor. In this example, the level of the seal is related to and can be inferred from a magnitude of the infrasonic signals.

The speaker is typically included in the housing body, and forms an acoustic seal with an inside wall of the housing body to prevent air and the biosignals from entering the housing body.

In another implementation, the speaker includes a sealed back portion that prevents air flow from the housing body into the speaker. Here, the speaker is an acoustically stiff speaker that has an effective acoustic volume that is on the order of or less than an acoustic volume of the inner ear canal.

In another implementation, the housing body includes a controlled port located between a top surface of the speaker and an inside wall of the housing body that enables air flow between the housing body and the nozzle. The housing body may further include a controlled opening filter placed in front of or within the controlled port, and the filter is configured to provide an impedance that prevents the biosignals from entering the housing body via the controlled port.

In another implementation, the housing body includes a distal port located at the distal end of the housing body. The distal port enables outside air flow into and out of the housing body. The housing body may further include a distal filter attached to an inside wall of the housing body and placed over or within the distal port. The distal filter is configured to provide an acoustic impedance that tunes the transmitted audio signals.

In general, according to another aspect, the invention features a method of operation of an earbud. The method checks for an acoustic seal between an earbud tip of the earbud and a wall of an inner ear canal of an individual, in response to insertion of the earbud tip in the wall of the inner ear canal. The method also detects biosignals including infrasonic signals from a body of the individual, via an infrasound/vibration sensor included within the earbud, where the biosignals are detected in the inner ear canal. The method also transmits sound from an audio source into the inner ear canal via a speaker included within the earbud.

In one implementation, the earbud checks for the acoustic seal via a pressure sensor included within the earbud. For this purpose, the pressure sensor senses a pressure in the inner ear canal, and the earbud determines whether the pressure is equal to or greater than a threshold amount. Alternatively, the infrasound/vibration sensor can check for the acoustic seal. The infrasound/vibration sensor detects the infrasonic signals of the biosignals, and the earbud determines whether a magnitude of the infrasonic signals is equal to or greater than a threshold amount. The acoustic seal increases body-generated acoustical pressure within the inner ear canal, which increases an amplitude of the biosignals in the inner ear canal.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 3A shows major components of the earbud and positioning of the earbud relative to the inner ear canal of the individual; FIG. 3B shows acoustic volumes created within the inner ear canal and within the earbud in response to operation of the earbud, and also illustrates a mechano-acoustical system formed by the biosignals and the acoustic volumes; and FIGS. 3C and 3D illustrate additional operational details of the earbud that could not be shown in the prior figures;

FIG. 5A shows major components of the earbud and positioning of the earbud relative to the inner ear canal of the individual; and FIG. 5B shows acoustic volumes created within the inner ear canal and within the earbud in response to operation of the earbud, where the figure also illustrates a mechano-acoustical system formed by the biosignals and the acoustic volumes;

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
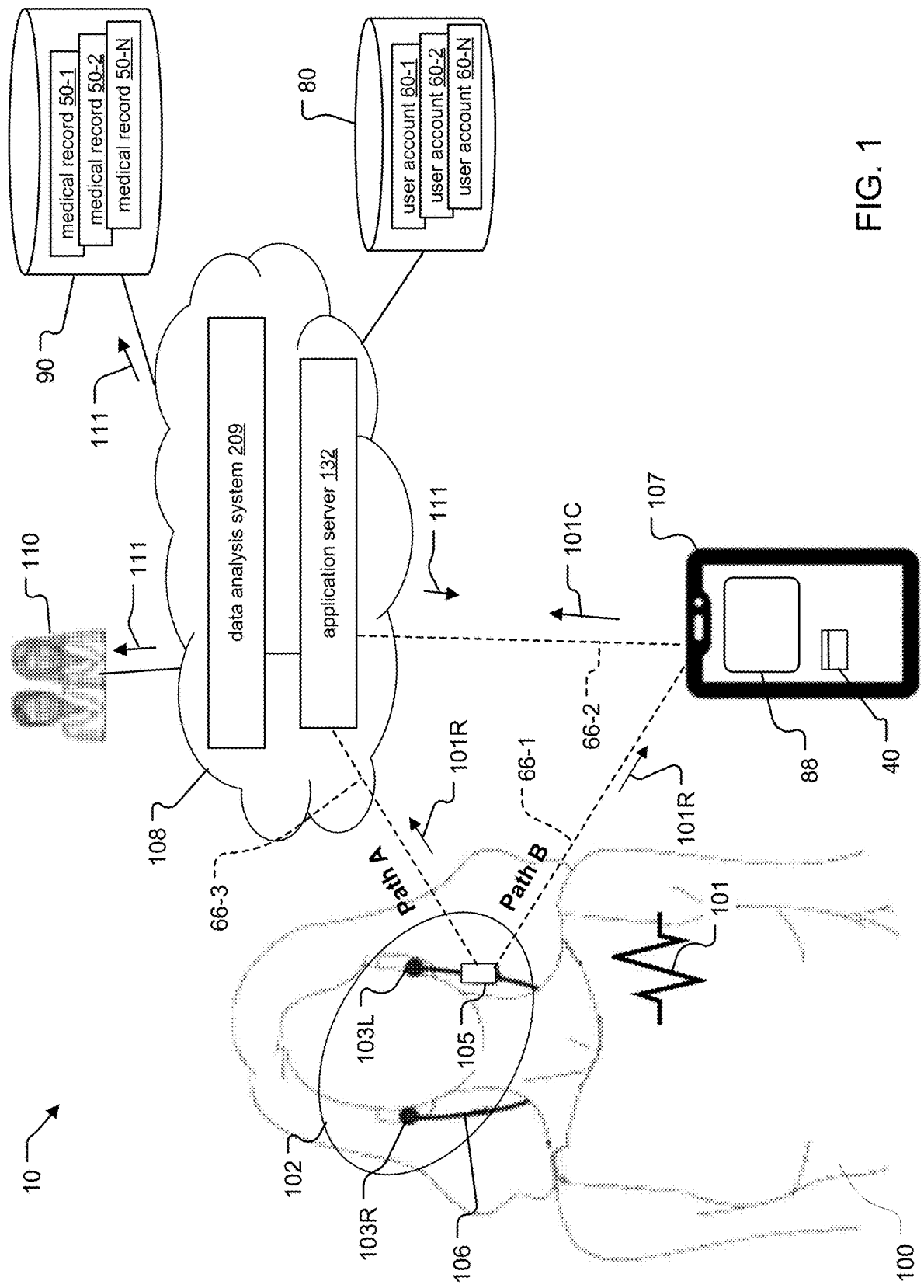
FIG. 1 is a schematic diagram of a health detection and analysis system ("health monitoring system") including an in-ear biosensor system worn by an individual, where the in-ear biosensor system includes at least one earbud constructed in accordance with principles of the present invention.

FIG. 1 shows an exemplary health detection and analysis system ("health monitoring system") 10. The health monitoring system 10 includes an in-ear biosensor system 102 worn by an individual 100 and a data analysis system 209.

The health monitoring system 10 also includes a user device 107 carried by the individual 100, an application server 132 located in a network cloud 108, and various databases that connect to the network cloud 108. The databases include a medical record database 90 and a user database 80. The medical record database 90 includes medical records 50 of individuals 100 and the user database 80 includes user accounts 60 of the individuals 100. The user accounts 60 are associated with individuals 100 that the system 10 determines are authorized users of the system 10.

The in-ear biosensor system 102 includes at least one earbud 103 placed at an inner ear canal of the individual 100 and a controller board 105. Preferably, as shown, the biosensor system 102 includes left and right earbuds 103L,R that each connect to the controller board 105 via separate earbud connections 106. Alternatively, the earbud connections 106 can be wireless connections. In implementations, the controller board 105 could be integrated within one of the earbuds 103 or across the earbuds 103L,R.

The controller board 105 includes non-volatile memory, a battery, a controller such as a microprocessor or microcontroller, and a network interface. The battery provides a source of power for the controller, the memory and the network interface. In one implementation, the battery might also provide a source of power to the earbuds 103.

The controller board 105 enables communications between the earbuds 103L, 103R via the network interface and the earbud connection 106. In one implementation, the network interface might include a wireless transceiver that communicates with wireless transceivers included within one or more of the earbuds 103. In this implementation, the physical earbud connection 106 is replaced with wireless links established between the controller board 105 and the earbuds 103.

The user device 107 is a computing device that includes a display 88 and at least one interactive application or user app 40. The user device 107 might be a mobile phone, a smart watch, or a laptop, in examples. The user app 40 executes upon a central processing unit (CPU) of the user device 107, receives information sent by other components in the system 10 and presents a graphical user interface (GUI) on the display 88. The GUI allows the individual 100 to enter information for the user app 40 and can display various information upon the display 88.

Medical professionals 110 are also shown. The medical professionals 110 include doctors nurses/nurse practitioners, physician's assistants, and medical technicians, in examples.

The application server 132 is a computing device that connects the biosensor system 102 and the user device 107 to the databases 80,90, the medical professionals 110 and the data analysis system 209. The application server 132 includes secure website software (or a secure proprietary application) that executes on the application server 132.

The medical professionals 110, the user database 80, the user devices 107 and the medical record database 90 can connect to the network cloud 108 and components within the cloud 108 in various ways. These connections can be wired Internet-based or telephony connections, wireless cellular connections, and/or wireless Internet-based connections (e.g. Wi-Fi), in examples. In examples, the network cloud 108 is a public network, such as the Internet, or a private network.

Infrasounds

Biosignals such as acoustic signals are generated internally in the body by breathing, heartbeat, coughing, muscle movement, swallowing, chewing, body motion, sneezing and blood flow, in examples. The acoustic signals can be also generated by external sources, such as air conditioning systems, vehicle interiors, various industrial processes, etc. The acoustic signals include audible and infrasonic signals.

The acoustic signals represent fluctuating pressure changes superimposed on the normal ambient pressure of the individual's body and can be defined by their spectral frequency components. Sounds with frequencies ranging from 20 Hz to 20 kHz represent those typically heard by humans and are designated as falling within the audible range. Sounds with frequencies below the audible range (i.e. from 0 Hz to 20 Hz) are termed infrasonic or infrasounds. The level of a sound is normally defined in terms of the magnitude of the pressure changes it represents. These changes can be measured and may depend on the frequency of the sound.

The health monitoring system 10 generally operates as follows. An individual 100 wearing the in-ear biosensor system 102 typically initiates a login procedure by accessing the user app 40 of the user device 107. The individual 100 enters his/her credentials in the user app 40, which in turn sends the credentials for authentication to the application server 132. The secure website software at the application server 132 compares the entered credentials to those stored within the user accounts 60 of authorized users of the system 10. Upon finding a match, the application server 132 establishes an authenticated, secure login session over wireless connection 66-2 between the user app 40 and the application server 132 for the individual as an authorized user of the system 10. Once the individual 100 is authenticated, the user app 40 establishes secure wireless connection 66-1 between the user device 107 and the controller board 105. The user app 40 then sends various commands over the wireless connection 66-1 to the controller board 105.

The earbuds 103L,103R continuously detect and collect biosignals 101 from a body of the individual 100. The earbuds 103 operate continuously when the in-ear biosensor system 102 is on, or at a time specified by either the individual 100 or the health monitoring system 10, in examples. The earbuds 103 convert the biosignals 101 into corresponding electrical signals that carry physiological data of the individual, and send the electrical signals to the controller board 105. Here, the electrical version of the biosignals 101 are typically in "raw" format: they are uncompressed and may include some noise and/or motion artifacts. The controller board 105 then buffers the electrical representation of the biosignals 101 for subsequent secure transmission to the data analysis system 209 for analysis.

The in-ear biosensor system 102, via its controller board 105, can send the electrical representation of the biosignals 101 to the data analysis system 209 by way of possibly different communications paths. These paths are labeled Path A and B in the figure. For convenience, the electrical versions of the biosignals 101 that the in-ear biosensor system 102 sends over the Paths A, B are simply referred to as biosignals in the remaining description that follows.

When using Path B, the controller board 105 sends raw versions of the biosignals 101R over link 66-1 to the user device 107. The user app 40 then compresses the signals 101R into compressed versions 101C of the signals for transmission over link 66-2 to the application server 132. The application server 132 then decompresses the compressed biosignals 101C and forwards the signals to the data analysis system 209.

When using Path A, the controller board 105 can send the raw biosignals 101R over link 66-3 to the application server 132 without having to compress the signals prior to transmission. This is because link 66-3 is typically a high-speed link such as a 5G cellular wireless link or 100 MB WiFi link, in examples. Here, the application server 132 can perform various operations on the raw biosignals 101R before forwarding the signals to the data analysis system 209 for analysis. These operations include filtering and characterization, authentication, and/or buffering of the signals, in examples.

The data analysis system 209 then analyzes the biosignals 101 to determine various physiological/heath conditions of the individual 100. For this purpose, the analysis system 209 identifies and/or extracts the physiological data carried within the signals 101, and determines the various physiological conditions of the individual 100 based upon the physiological data. The analysis system 209 can then update a medical record 50 of the individual 100 in response to the analysis, notify the individual 100 of possible conditions that may impact their health, and can also notify the medical professionals 110 of the conditions. For this purpose, the data analysis system 209 can send notification messages 111 that include the updates to the medical records 50, the information sent to the medical professionals 110, and possibly to the individuals 100.

Figure 2A:
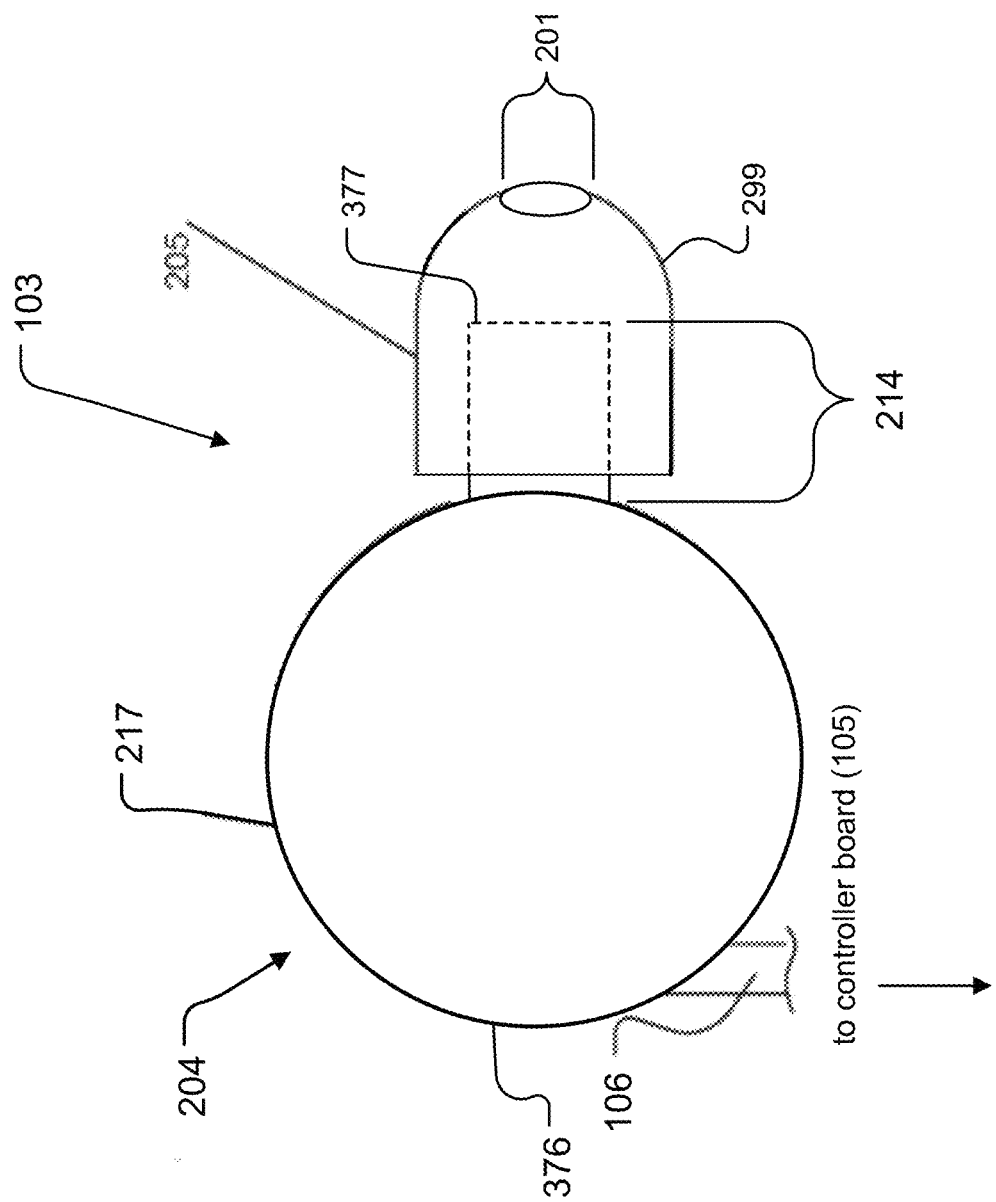
FIG. 2A is a schematic diagram of an exemplary earbud in the in-ear biosensor system of FIG. 1.

FIG. 2A shows major components of an exemplary earbud 103. These components include a housing 204, a nozzle 214 and a body 217 of the housing 204 (housing body 217), an earbud connection 106 and an earbud tip 205. In the illustrated example, much of the nozzle 214 is shown in phantom.

The housing 204 has a distal end 376 and the nozzle has a proximal end 377. The nozzle 214 either attaches to or is formed at a side of the housing body 217 such that the proximal end of the nozzle 377 is opposite to the distal end 376 of the housing 204/housing body 217. The nozzle 214 thus extends outward from the housing body 217. Generally, the nozzle 214 is cylindrical in shape, and the housing body is spherical in shape. However, other shapes for the nozzle 214 and the housing body 217 are possible.

The earbud tip 205 attaches to the nozzle 214 at the proximal end 377 of the nozzle 214. The earbud tip 205 has an opening 201 and a face 299 that is configured for placement in an inner ear canal of the individual 100.

The nozzle 214, the housing body 217 and the earbud tip 205 can be constructed or arranged in different ways. In one implementation, the nozzle 214, the housing 204/housing body 217 and the earbud tip 205 are separate components. The earbud tip 205 attaches to the proximal end 377 of the nozzle 214, and the end of the nozzle 214 opposite its proximal end 377 attaches to the housing 204/housing body 217.

In another implementation, as shown, the nozzle 214 and the housing body 217 are formed from a unitary piece of material to create the housing 204, and the separate earbud tip 205 attaches to the proximal end 377 of the nozzle 214.

In examples, the material of the housing 204 can be plastic, metal, rubber, a carbon-based material, or some combination of these materials.

In yet another implementation, the nozzle 214 and the earbud tip 205 are combined into/formed as a single component or assembly that then attaches to the separate housing body 217. Here, the combined nozzle 214 and earbud tip 205 might be formed from the same material such as acoustically-compliant foam, plastic, metal, rubber, a carbon-based material, or some combination of these materials. A side of the combined assembly that is opposite to the proximal end of the nozzle 214 then attaches to the housing body 217.

In the illustrated example, the earbud 103 connects to the controller board 105 (not shown) via earbud connection 106. The earbud connection 106 is a cable that includes multiple wires that connect the controller board 105 to various components of the earbud 103. Some of the wires enable communications such as the transfer of control and data signals between the earbuds 103 and the controller board 105. Other wires provide power to the earbuds. In one implementation, the housing body 217 additionally includes a local battery that provides a local source of power to the earbuds 103.

In another implementation, the earbud connection 106 is a wireless connection. In this example, the earbuds 103 each include a local battery and a wireless transceiver that communicates with a wireless transceiver of the controller board 105. The battery provides a source of power to the components within each earbud, including the wireless transceiver. The transceiver then communicates the data and control signals over wireless links to the wireless transceiver of the controller board 105.

In yet another implementation, the controller board 105 is incorporated within one or both earbuds. In this way, the earbuds 103 form an all-wireless version of the in-ear biosensor system 102.

Figure 2B:
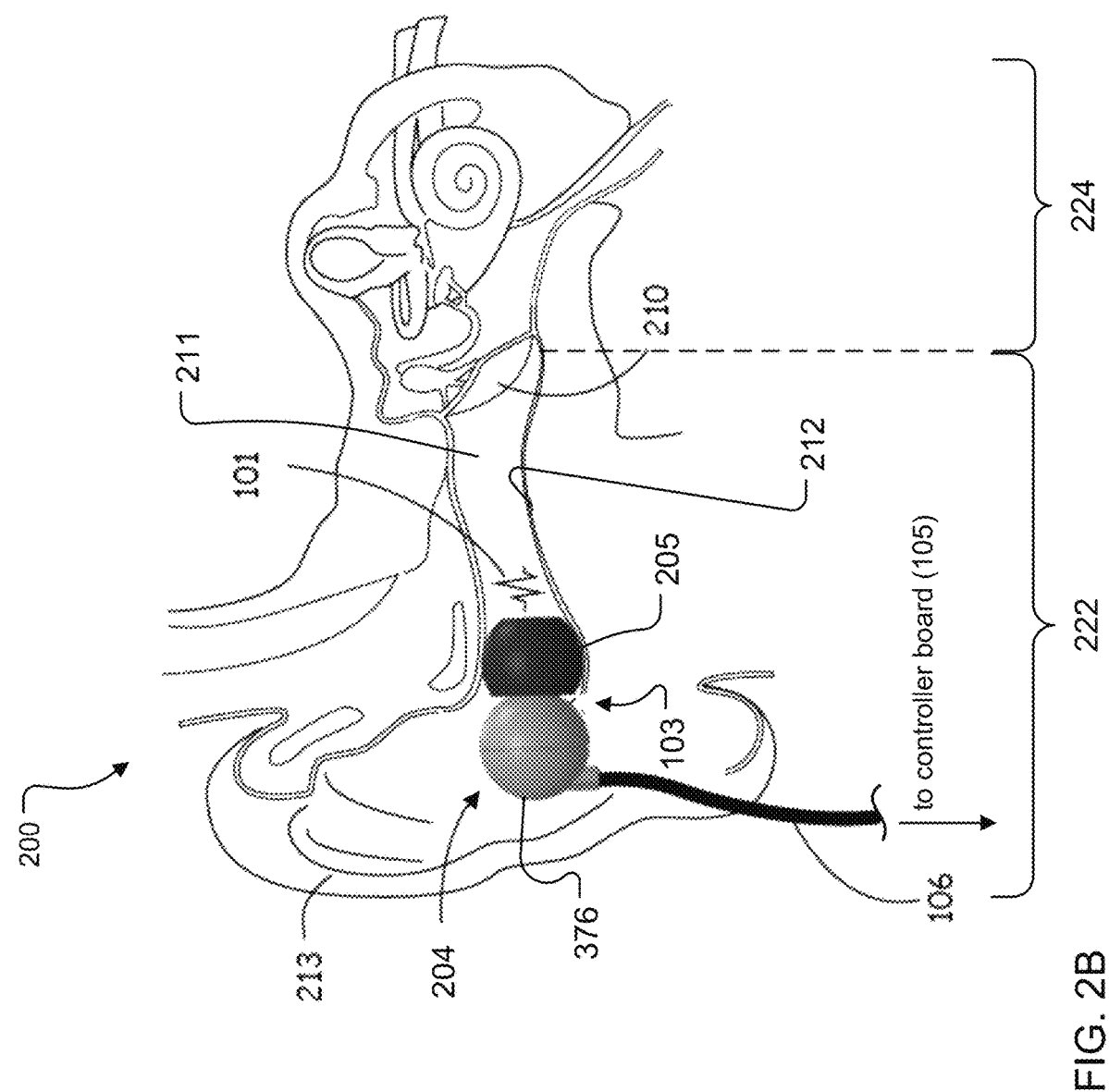
FIG. 2B is a cross-sectional anatomical depiction of an individual's ear, where an earbud placed within an inner ear canal of the ear is shown.

FIG. 2B is a non-limiting example of placement of the earbud 103 within a human ear 200. The ear 200 has an external portion 222 and middle and inner portions, the latter two of which are indicated by reference 224. Major components of the external portion 222 include a pinna 213, an inner ear canal 211 and a tympanic membrane 210.

Exemplary earbud 103 is shown in the figure. The earbud tip 205 is positioned at/within the inner ear canal 211 to enable the earbud 103 to detect the biosignals 101 from the individual 100.

By way of background, the human body generates mechanical vibrations and/or acoustic waves that travel through different media in the body such as the blood vessels, bones, muscles, tissue and cartilage. Such vibrations produced by the human body may be sensed by different transducers and/or vibration sensors attached at different parts of the body, for example, as in seismocardiography and ballistocardiography. The earbuds 103 detect these mechanical vibrations and/or acoustic waves via one or more sensors included within the left and right earbuds 103L, R.

Because the earbud tips 205 of the earbuds 103 seal the opening to the inner ear canal 211, pressure inside the ear canal can build up/increase, and the body vibrations can be trapped inside the inner ear canal 211 and possibly also within the earbud 103. This increase in pressure can amplify the vibrations, especially the low frequency infrasound vibrations described above. This relationship may be characterized by the following equation:

$$P = Va*Za, \text{ where}$$

P=Acoustic pressure within the ear canal, in Pascals
Va=Acoustic volume velocity of the air in the canal, in $m^3/sec$, and
Za=Acoustic impedance looking out from the ear canal towards free space ($Pa*sec/m^3$).

By way of example, human body vibrations associated with the cardiovascular system of the individual may be generated in the frequency range 0-25 Hz, with a majority of the signal in the range of 0 to 5 Hz. Such vibrations have a wavelength varying from 13 m to 3.3 km in air at about 20 C.

As these wavelengths are considerably longer than any ear dimension, it may be said that these are relatively low frequencies. At low frequencies the acoustic impedance looking out of an open ear canal is negligible, but as the ear canal is occluded and sealed the acoustic impedance becomes proportional to $$Z_{cavity} \approx \frac{\rho C^2}{\text{Volume}},$$

where
Zcavity=Acoustic impedance of a sealed cavity
$\rho$=the density of air (1.21 $kg/m^3$)
C=the speed of sound in air (342 m/sec), and
Volume=the volume of the cavity, in $m^3$.

As the inner ear canal volume decreases with increasing occlusion and seal, the impedance of the ear canal cavity, Za, increases. As a result, for a given volume velocity Va, caused by the body, the pressure will increase relative to the inner ear canal.

As an additional non-limiting example, one form of the ideal gas law states that $$P_1 * V_1 = P_2 * V_2, \text{ where}$$

P1=Initial body-generated acoustic pressure in the unoccluded ear canal, in Pa
V1=Initial volume of the unoccluded ear canal, in $m^3$
P2=Acoustic pressure in the Occluded ear canal, in Pa
V2=Volume of the Occluded ear canal, in $m^3$ The volume of the unoccluded inner ear canal 211 is quite large. This volume approaches infinity when looking from the inner ear canal 211 towards the pinna 213 and out into free space. In contrast, the volume of the occluded ear canal is on the order of 2 cc. This tremendous decrease from V1 to V2 accounts for a correspondingly large increase from P1 to P2. Note that a decrease from 200 cc to 2 cc would increase the pressure by 40 dB.

Figure 3A:
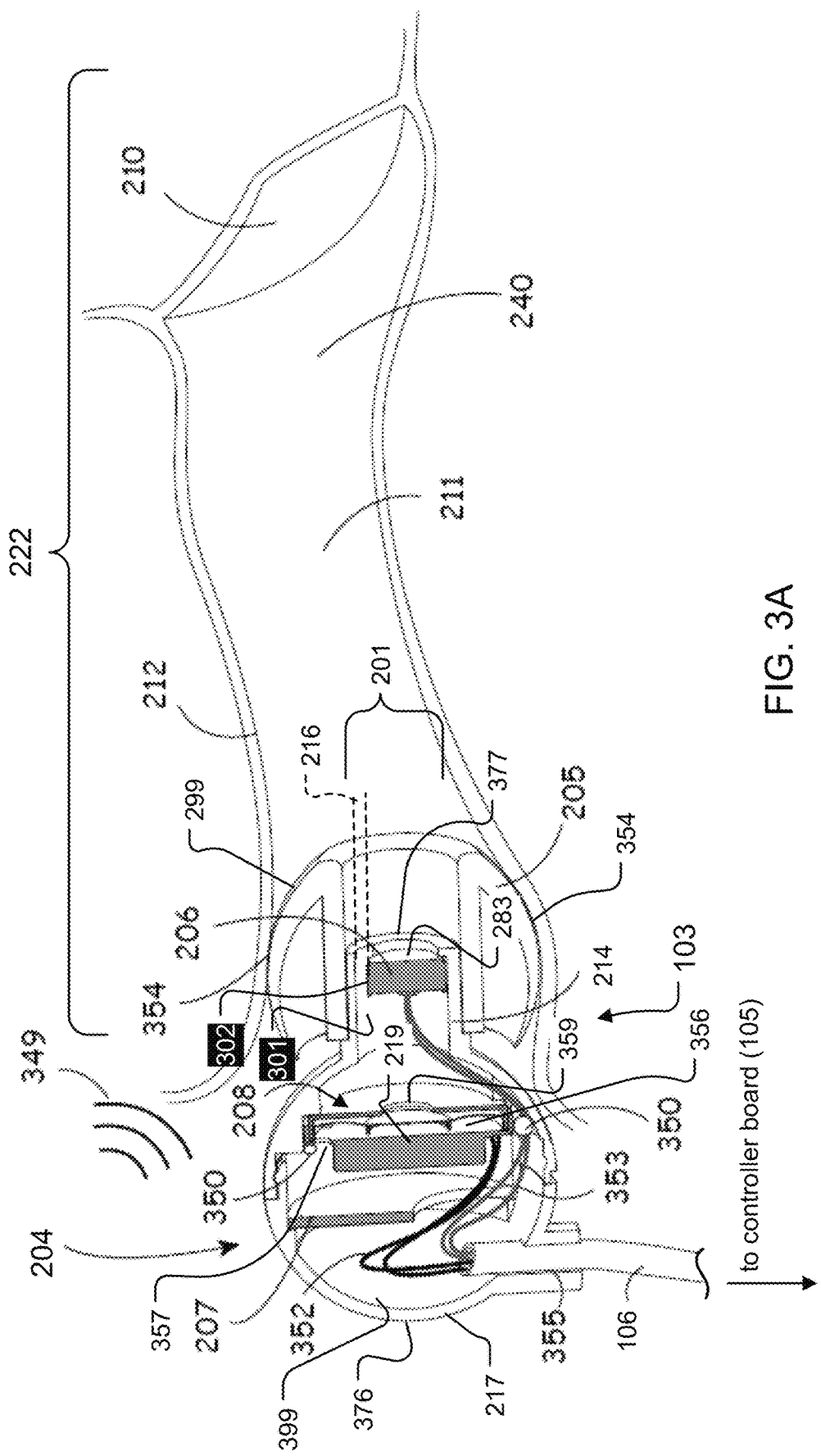
FIG. 3A-3D are cutaway views of an earbud, according to an embodiment, as deployed in a cross-sectional anatomical depiction of an individual's ear, and where.

FIG. 3A shows a preferred embodiment of an earbud 103 in the health monitoring system 10 of FIG. 1. In the illustrated example, the earbud 103 is positioned at/within the external portion 222 of an individual's ear. The earbud 103 and the external portion 222 of the ear are shown in cross-section to show components of/within the earbud 103, and to enable description of the components with respect to the external ear portion 222. To improve the illustration and description of the earbud 103, the pinna 213 of the external ear portion 222 is not shown.

The earbud 103 includes various components within the housing body 217 and/or nozzle 214. These components include a speaker 208, a printed circuit board 207, an acoustic sensor such as an infrasonic/vibration sensor 206, and other sensors including a pressure sensor, a motion sensor, and possibly even a temperature sensor. The motion sensor might be an accelererometer, a gyroscope, or a combination of these devices. The pressure sensor, the temperature sensor and the motion sensor are not shown in the figure.

The earbud tip 205 has a face 299 that is designed to engage the inner ear canal 211. This allows the earbud 103 to remain in the individual's ear. For this purpose, the individual 100 places the earbud tip 205 within the individual's ear such that the face 299 is inserted at/within wall 212 of the inner ear canal 211.

The earbud tip 205 also forms an airtight seal 354 between the face 299 of the earbud tip 205 and the wall 212 of the inner ear canal 211. To provide this seal 354, the tip 205 is generally spherical in shape and is formed from a pliable material that enables a snug fit of the tip 205 in the inner ear canal 211. The material might be silicone, foam such as memory or acoustical foam, or rubber, in examples.

The seal 354 has the following benefits. First, it prevents air from entering the ear canal 211, and can significantly attenuate external sounds that might otherwise interfere with the biosignals 101. The seal 354 also enables pressure to build up/increase within the inner ear canal. This increase in pressure forms an acoustic volume within the inner ear canal 211 that can significantly amplify/increase the amplitude of the biosignals 101 within the inner ear canal 211. At the same time, this pressure increase is also harmless to the individual 100.

The material of the earbud tip 205 also impacts the seal 354 and the ability of the earbud 103 to detect the biosignals 101. During operation of the earbuds 103, the biosignals 101 within the inner ear canal strike the earbud tip 205, causing the tip to vibrate. If the material that forms the earbud tip 205 is too acoustically compliant, the earbud tip 205 might vibrate enough to cause the level of the seal 354 to degrade. This lowers the pressure in the inner ear canal/reduces its acoustic volume, and thus reduces the amplitude of the biosignals 101 that can be detected in the inner ear canal 211. As a result, a more rigid/acoustically stiff material is typically selected for the earbud tip 205 to minimize the vibrations of the earbud tip 205, and thus to maximize the seal 354, constraining the acoustic volume of the inner ear canal 211, and maximizing the amplitude of the biosignals 101.

The earbud tip 205 attaches to the nozzle 214. The tip 205 typically attaches to the nozzle 214 using a fit such as a press fit or a friction fit. This attachment enables the nozzle 214 to be suspended within the inner ear canal 211 when the earbud tip 205 is engaged with the ear canal 211/wall 212 of the ear canal 211.

The speaker 208 has a back portion 219 and a diaphragm 356. The back portion 219 may be mounted to the printed circuit board 207, and the diaphragm 356 faces outward toward the nozzle 214. The speaker 208 is also sealed within the housing body 217, indicated via reference 350. The back portion 219 also has an opening that opens into the housing body 217.

The printed circuit board 207 is included within the housing body 217. The printed circuit board 207 is fastened to an inner surface 399 of the housing body 217 and enables rigid attachment of the speaker 208 to the printed circuit board 207. The diaphragm 356 is also sealed from front to back due to the mounting of the speaker 208 to the board 207.

The earbud 103 might also include a local microcontroller and a battery mounted to the printed circuit board 207. The microcontroller has local memory and is powered by the battery. The microcontroller can receive information from the pressure sensor and the infrasonic/vibration sensor 206 and pre-process this information before sending the information via the earbud connection 106. For example, the microcontroller might assess a leak level of the acoustic seal 354 based upon the information detected by and sent from the pressure sensor and/or the infrasound/vibration sensor 206. In one implementation, the microcontroller is implemented using custom logic programmed into an application-specific integrated circuit (ASIC) component or chip.

In yet another example, the controller board 105 is included within one or more of the earbuds 103. Here, the controller board 105 is the printed circuit board 207.

Connections between the controller board 105 (not shown in the figure) and the earbud 103 are also shown. Speaker wires 352 and sensor wires 353 of the earbud connection 106 connect to the speaker 208 and the sensors, such as the illustrated infrasonic/vibration sensor 206. A cable seal 355 is also formed between the housing body 217 and the earbud connection 106 to eliminate air and external sounds 349 from entering the housing 204.

The nozzle 214 typically includes the infrasonic/vibration sensor 206 and the pressure sensor (not shown). The infrasonic/vibration sensor 206 is preferably located at the proximal end 377 of the nozzle 214 and attaches to an inside wall 301 of the nozzle 214. The infrasonic/vibration sensor 206 faces the inner ear canal 211 and substantially encloses the nozzle 214 at or near the proximal end 377 of the nozzle 214.

The pressure sensor can monitor the acoustic seal 354 or provide static pressure as a baseline for the biosignals 101 detected by the infrasound/vibration sensor 206. Alternatively, the acoustic seal 354 could be monitored using the infrasound/vibration sensor 206. In this example, the level of the seal 354 is related to and can be inferred from a magnitude of the infrasonic signals of the biosignals 101.

The nozzle 214 also includes an opening or port 216 at the proximal end 377 of the nozzle 214. In the illustrated example, the port 216 is a gap within the nozzle 214 between a top surface 302 of the infrasonic/vibration sensor 206 and the inside wall 301 of the nozzle 214.

In another implementation, the port 216 is a tube inserted into an otherwise sealed proximal end 377 of the nozzle 214. Here, the sealed end is formed by the infrasonic/vibration sensor 206 and a material that fills the gap within the nozzle 214 between the top surface 302 of the sensor 206 and the inside wall 301 of the nozzle 214.

The earbud 103 generally operates as follows. Biosignals 101 including infrasonic signals from the body of the individual 100 exit the body of the individual 100 via the wall 212 and enter the inner ear canal 211. The seal 354 enables the pressure in the inner ear canal 211 to increase and thus decreases the acoustic volume of the inner ear canal 211. This, in turn, increases the amplitude of the biosignals 101 in the acoustic volume. In this way, the amplitude of the biosignals is significantly increased prior to the earbud 103 detecting the biosignals 101 in the inner ear canal 211.

The biosignals 101 then enter the opening 201 of the earbud tip 205 and impinge upon a detection face 283 of the infrasonic/vibration sensor 206. The infrasonic/vibration sensor 206 detects the biosignals 101 and sends an electronic representation of the signals via the earbud connector 106 to the controller board 105. The controller board 105 buffers the signals and sends the signals 101 over one or more of the wireless links 66 to the data analysis system 209 for analysis and reporting.

At the same time, the speaker 208 receives audio signals from an audio source via the speaker wires 352. The speaker 208 converts the signals into sound waves via the diaphragm 356 of the speaker. Reference 359 indicates a vibration of the diaphragm 356 during this process. The speaker 208 transmits the sound into the nozzle 214 and in the direction of the inner ear canal 211. The transmitted sound exits the nozzle 214 via the nozzle port 216 and leaves the earbud 103 through the earbud tip opening 201, and enters the inner ear canal 211. The tympanic membrane 210 then vibrates in response to the transmitted sound waves.

Figure 3B:
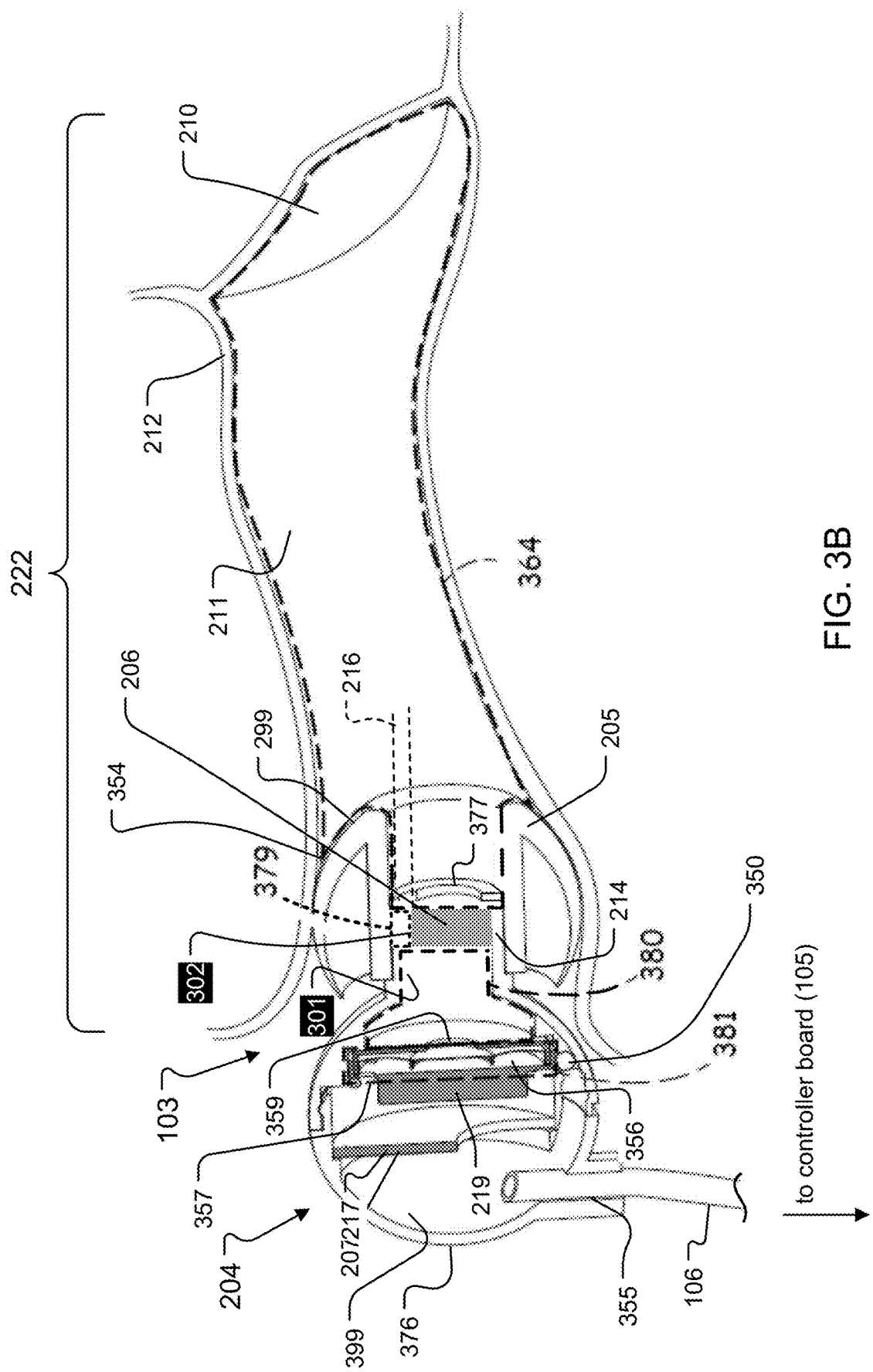

FIG. 3B provides more detail for the embodiment of the earbud 103 in FIG. 3A.

The seal 350 of the speaker has multiple purposes. It prevents sound waves generated by the rearward-facing surface of the diaphragm 356 interacting with sound waves generated at the front-facing surface of the diaphragm 356. The seal 350 also prevents any biosignals 101 that may enter the nozzle 214 from traveling further into the nozzle 214 and entering the housing body 217.

An opening 357 in the back portion 219 of the speaker 208 is also shown. The opening 357 enables airflow between the back of the diaphragm 356 and the housing body 217. The airflow provided by the opening 357 allows the diaphragm 356 to vibrate more than a speaker with a closed back portion 219 can. As a result, the speaker 208 may be considered to be an acoustically compliant speaker.

The acoustic volume of the inner ear canal 211 that was described in FIG. 3A is indicated by reference 364. However, this is not the only acoustic volume that designers of the earbud 103 must consider. In addition, the earbud 103 itself has an overall acoustic volume associated with components of the earbud 103 that forms during operation of the earbud 103.

The acoustic volume of the earbud 103 is a sum of individual effective acoustic volumes of components within the earbud 103, and acoustic volumes formed in spaces/cavities within the housing 204 and/or nozzle 214 through which sound can propagate. These acoustic volumes include an effective acoustic volume 381 of the speaker 208, an inter-housing acoustic volume 380, and a small, upper acoustic volume 379.

From an impedance point of view, these acoustic volumes are in parallel-series combination, resulting in an equivalent acoustic volume that is proportional to the sum of: (ear canal acoustic volume 364+speaker effective acoustic volume 381+inter-housing acoustic volume 380+upper acoustic volume 379). The speaker effective acoustic volume 381 accounts for the acoustic volume produced by the operation of the speaker 208 at its installed location in the housing body 217. The inter-housing acoustic volume 380 is formed in a space between the between the diaphragm 356 and the infrasonic/vibration sensor 206. The upper acoustic volume 379, that connects the inner ear canal volume 364 with the speaker and inter-housing acoustic volume 380, is formed in the gap between the top surface 302 of the sensor 206 and the (top) inside wall 301 of the nozzle 214.

Designers must design the earbud and its components so that the acoustic volume of the earbud 103 does not significantly increase the ear canal acoustic volume 364. This is because the amplitude of biosignals 101 in the inner ear canal 211 generally increases as the inner ear acoustic volume 364 decreases. In general, the acoustically compliant speaker 208 is designed so that its effective acoustic volume 381 is equal to or greater than the inner ear canal acoustic volume 364. Typically, the acoustic volume of an average individual's inner ear canal is about 2 cubic centimeters (2 cc).

The figure also illustrates a mechano-acoustical system formed by the biosignals 101 and the acoustic volumes 364, 379, 380 and 381. Using principles of duality, designers can model behavior of the mechano-acoustical system by creating an equivalent electrical circuit, in one example.

Figure 3C:
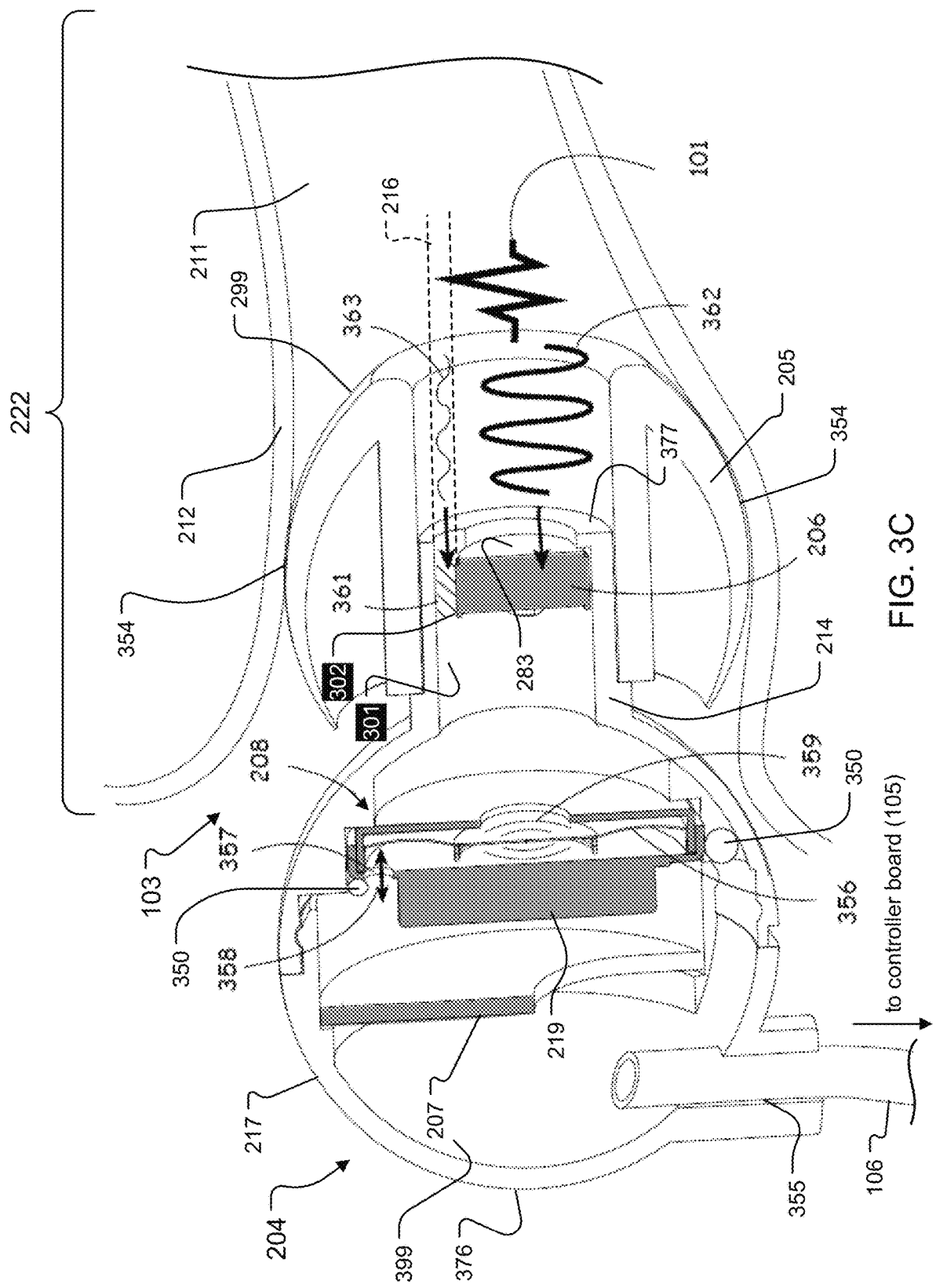

FIG. 3C illustrates more aspects of the earbud 103 shown in FIGS. 3A and 3B. Here, the figure shows how the earbud 103 can effectively prevent infrasonic signals of the biosignals 101 from entering the nozzle 214 via the port 216. The infrasonic signals include original or "high amplitude" versions 362 of the infrasonic signals, and attenuated versions 363 of the infrasonic signals. The figure also shows more detail for the opening 357 first introduced in FIG. 3B.

The infrasonic/vibration sensor 206 detects the high amplitude versions 362 of the infrasonic signals that impinge upon the detection face 283 of the infrasonic/vibration sensor 206. The infrasonic/vibration sensor 206 then sends electrical representations of the infrasonic signals 362 via the earbud connection 106 to the controller board 105.

The ability of the earbud 103 to effectively prevent infrasonic signals of the biosignals 101 from entering the nozzle 214 is accomplished via an acoustic impedance 361 of the port 216. The acoustic impedance 361 is sufficiently high, such that the otherwise high amplitude 362 infrasonic signals are significantly attenuated at the port 216. This is illustrated by the attenuated versions 363 of the infrasonic signals in the figure.

Without the acoustic impedance 361 provided by the port 216, some of the high amplitude 362 infrasonic signals might enter the nozzle 214 via the port 216. This is essentially an acoustic leak; the infrasonic signal simply dissipates into the apparently larger volume so that its amplitude is reduced.

In contrast, the port 216 allows only some attenuated versions 363 of the infrasonic signals to enter the nozzle 214. Experimentation has shown that the relatively small number of attenuated versions 363 of the signals that enter the nozzle 214, in conjunction with their small amplitudes, has a negligible effect upon the sound waves transmitted by the speaker 208.

The opening 357 in the back portion 219 of the speaker 208 is also shown in more detail. The opening 357 allows air flow 358 both into and out of the back portion 219 of the speaker 208.

Figure 3D:
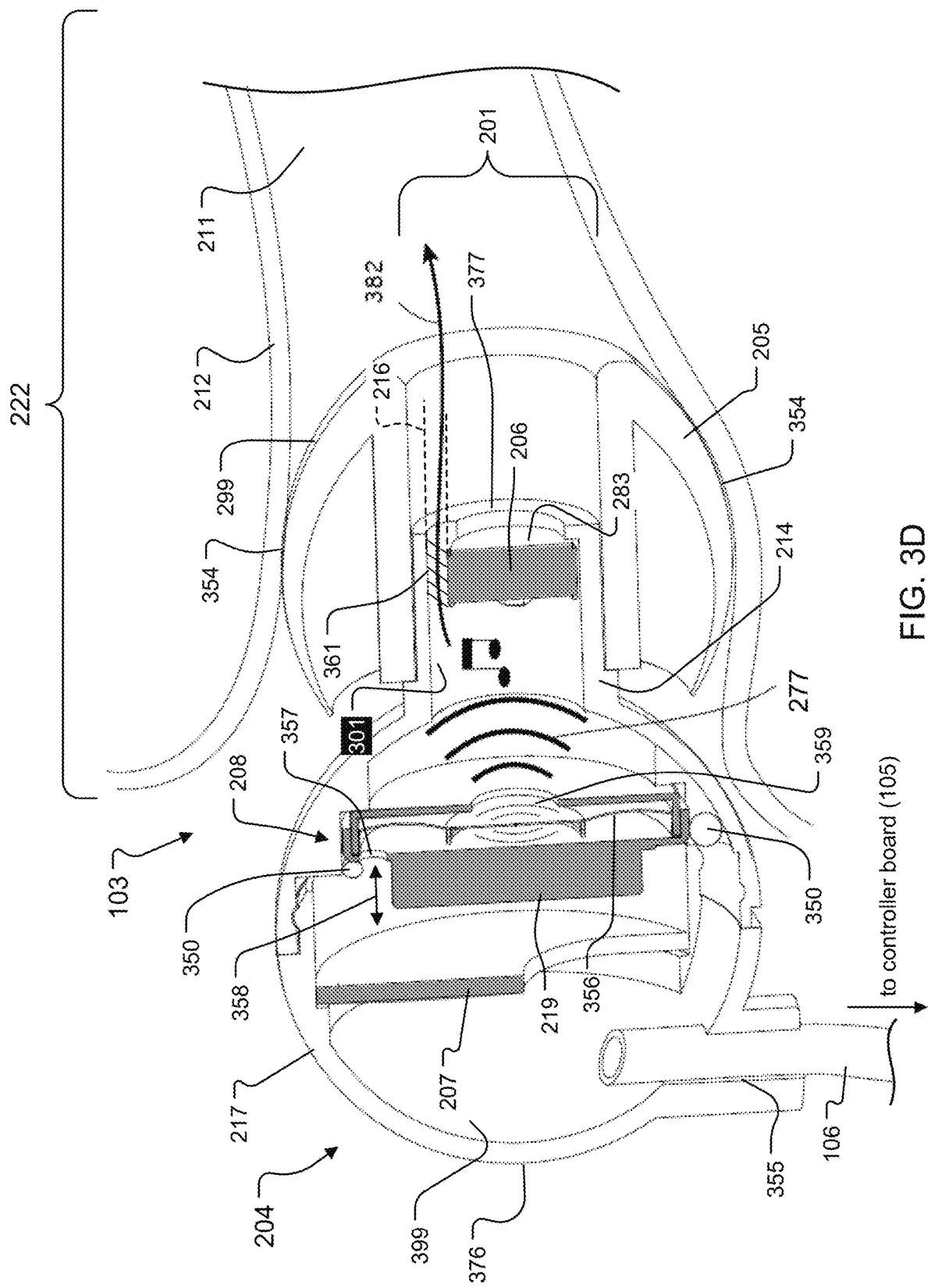

FIG. 3D illustrates some aspects of the earbud 103 shown in FIG. 3A-3C in more detail. In the illustrated example, audio signals 277 transmitted by the speaker 208 are shown, and reference 382 indicates the direction of transmission of the signals 277 from the speaker 208 and into the inner ear canal 211.

In more detail, the vibration 359 of the diaphragm 356 causes the audio signals 277 to be transmitted in the space outside the diaphragm 356. In the example, the space is a cavity between the housing body 217 and the nozzle 214. The audio signals 277 then propagate in the direction of transmission 382 towards the proximal end 377 of the nozzle 214.

At the proximal end 377 of the nozzle 214, the port 216 allows the signals 277 to exit the nozzle 214. For this purpose, the acoustic impedance 361 of the port is designed/"tuned" to pass the acoustic signals 277 out of the port 216 with minimum modification. The signals 277 can then pass through the earbud opening 201 and into the inner ear canal 211.

As the compliance of the speaker 208 increases, the impedance 361 of the port 216 must be relatively high in order to maintain the effect of the acoustic seal 354. With reference to FIG. 3B, the upper acoustic volume 379, the inter-housing acoustic volume 380, and the speaker effective acoustic volume 381 must maintain a combined impedance that is equal to or grater than the ear canal impedance. However, the port 216 must be sufficiently short in length so that treble of the transmitted sounds 277 is not cut off by the low-pass filter caused by the acoustic mass of port 216. As a result, the port 216 must have the shortest length possible and maximum open area possible (both to minimize acoustic mass), and the open area must typically be covered or filled with an acoustically resistive material.

Figure 4:
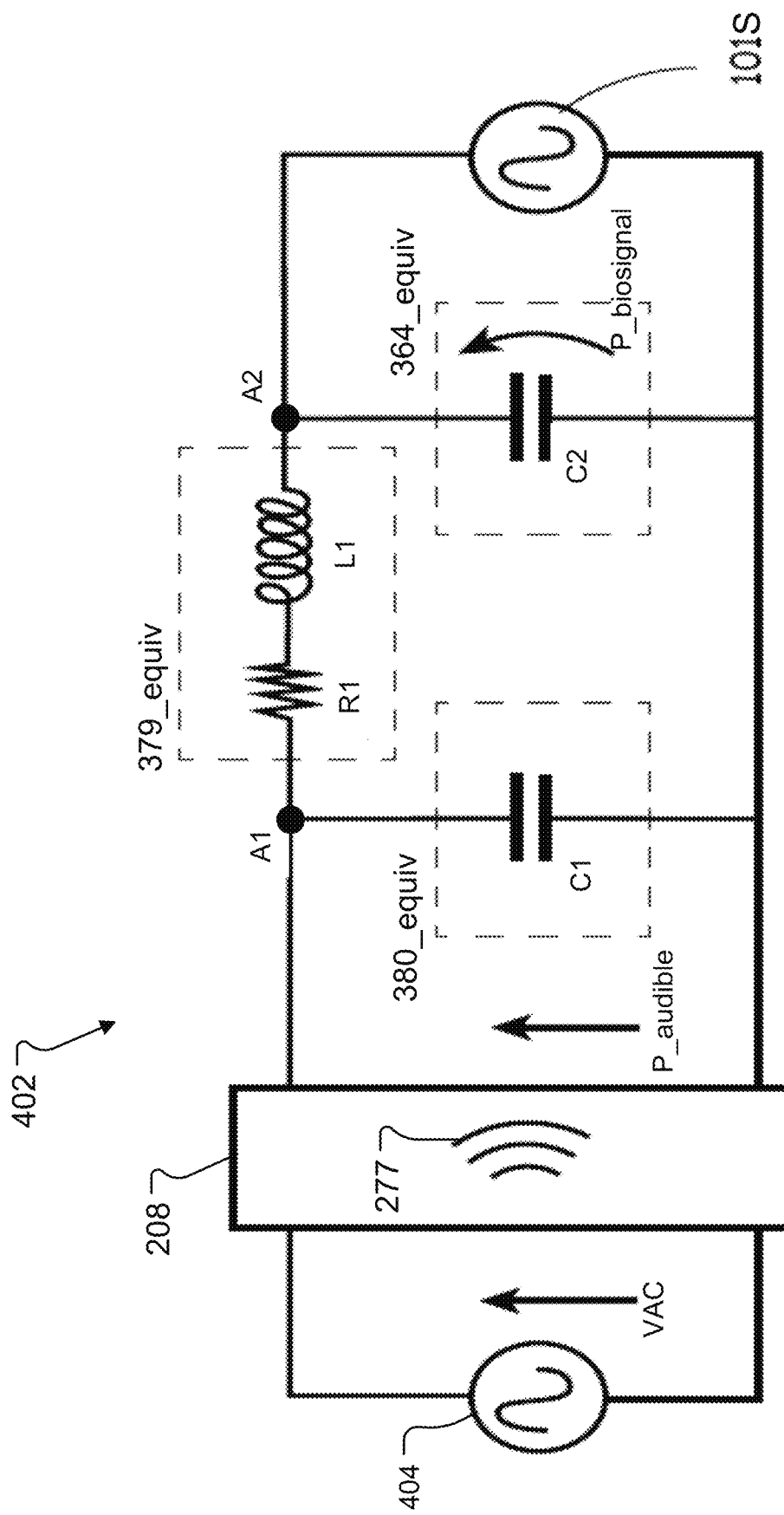
FIG. 4 is an equivalent electrical circuit for the mechano-acoustical system of FIG. 3B, where the electrical circuit models behavior of and components within the mechano-acoustical system using principles of duality.

FIG. 4 is an equivalent electrical circuit 402 for the mechano-acoustical system of the earbud 103 described in FIG. 3B. The electrical circuit 402 models behavior of and components within the mechano-acoustical system using principles of duality.

The circuit 402 includes various circuit components that "map" to corresponding components and acoustic volumes in FIG. 3B. These circuit components include an alternating voltage source 404, the speaker 208, capacitors C1 and C2, resistor R1 and inductor L1, and biosignal source 101S. Two parallalel circuit branches indicated by references A1 and A2 and a series portion located between the branches A1 and A2 are also shown.

The mechano-acoustical system of the earbud 103 maps to the circuit 402 as follows. The voltage from the audio source 277 is modeled as the alternating voltage source 404. The direction of the voltage is indicated by VAC. The pressure created by the speaker 208, and its direction, is indicated by reference P_audible. The effective acoustic volume of the speaker is incorporated within the speaker model 208. The pressure that the biosignals 101 add to the ear canal 364 is indicated by reference P_biosignal. This pressure is generated by the physiological biosignal source 101S.

The upper acoustic volume 379 is modeled as the series circuit portion of the circuit 402, indicated by reference "379 equiv." Here, the series circuit portion includes resistor R1 and inductor L1. The inter-housing acoustic volume 380 is modeled as parallel branch A1 and is indicated by reference "380 equiv." The circuit branch A1 includes capacitor C1. In a similar vein, the ear canal acoustic volume 364 is modeled as parallel branch A2 and is indicated by reference "364 equiv." The circuit branch A2 includes capacitor C2.

Figure 5A:
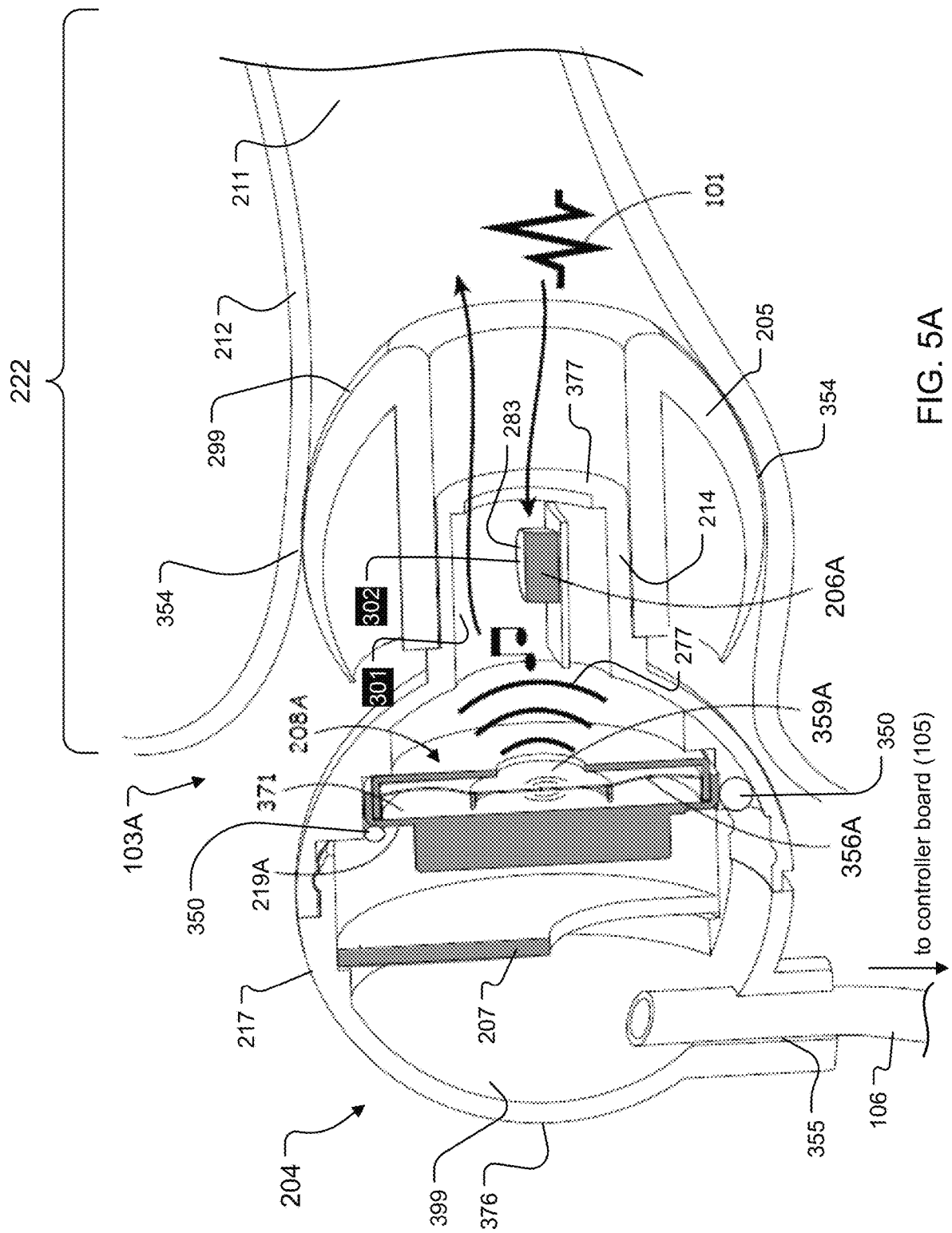
FIGS. 5A and 5B are cutaway views of an earbud, according to another embodiment, as deployed in a cross-sectional anatomical depiction of an individual's ear, and where.

FIG. 5A shows another earbud embodiment, earbud 103A. The earbud 103A includes substantially similar components as the earbud 103 shown in FIGS. 3A-3D and operates in a similar way. However, there are differences.

As in the earbud 103 of FIG. 3A-3D, the seal 354 of the earbud 103A against the wall 212 allows pressure to build in the inner ear canal 211 and around the infrasonic/vibration sensor. This amplifies the biosignals 101 in the ear canal 211 that are detected by the infrasound sensor. The transmitted audio signal 277 from the speaker also travels through the nozzle 214 and enters the inner ear canal 211.

In contrast, the earbud 103A includes a stiffer speaker 208A with a closed back portion 219A and a different arrangement of the infrasound/vibration sensor, indicated by reference 206A. The arrangement of the infrasound/vibration sensor 206A eliminates the port 216 as compared to the earbud 103 of FIG. 3A-3D.

In the illustrated example, speaker 208A is an acoustically stiff speaker that forms a stiff electro-mechano-acoustical effective component. Stiffness is the inverse of compliance (compliance=1/stiffness). Moreover, stiffness of a cavity is inversely proportional to the volume of the cavity (stiffness~1/volume), hence compliance is proportional to equivalent volume. With speakers such as 208A, the equivalent stiffness includes a mechano-acoustical transformation ratio (the radiating area, or equivalent piston area). The diaphragm 356A of the speaker 208A generally vibrates less than that of the speaker 208 of earbud 103, indicated by reference 359A. The speaker 208A is also sealed with respect to the housing body 217 via seal 350.

The infrasound/vibration sensor 206A is instead arranged such that its detection face now faces possibly in any direction. In the illustrated example, the detection face 283 points upward/is parallel to a plane of the ground or floor. Here, the biosignals 101 can freely enter the nozzle 214 (there is no "port" as in earbud 103) while the transmitted audio signals 277 simultaneously travel out through the nozzle 214 and into the inner ear canal 211.

Figure 5B:
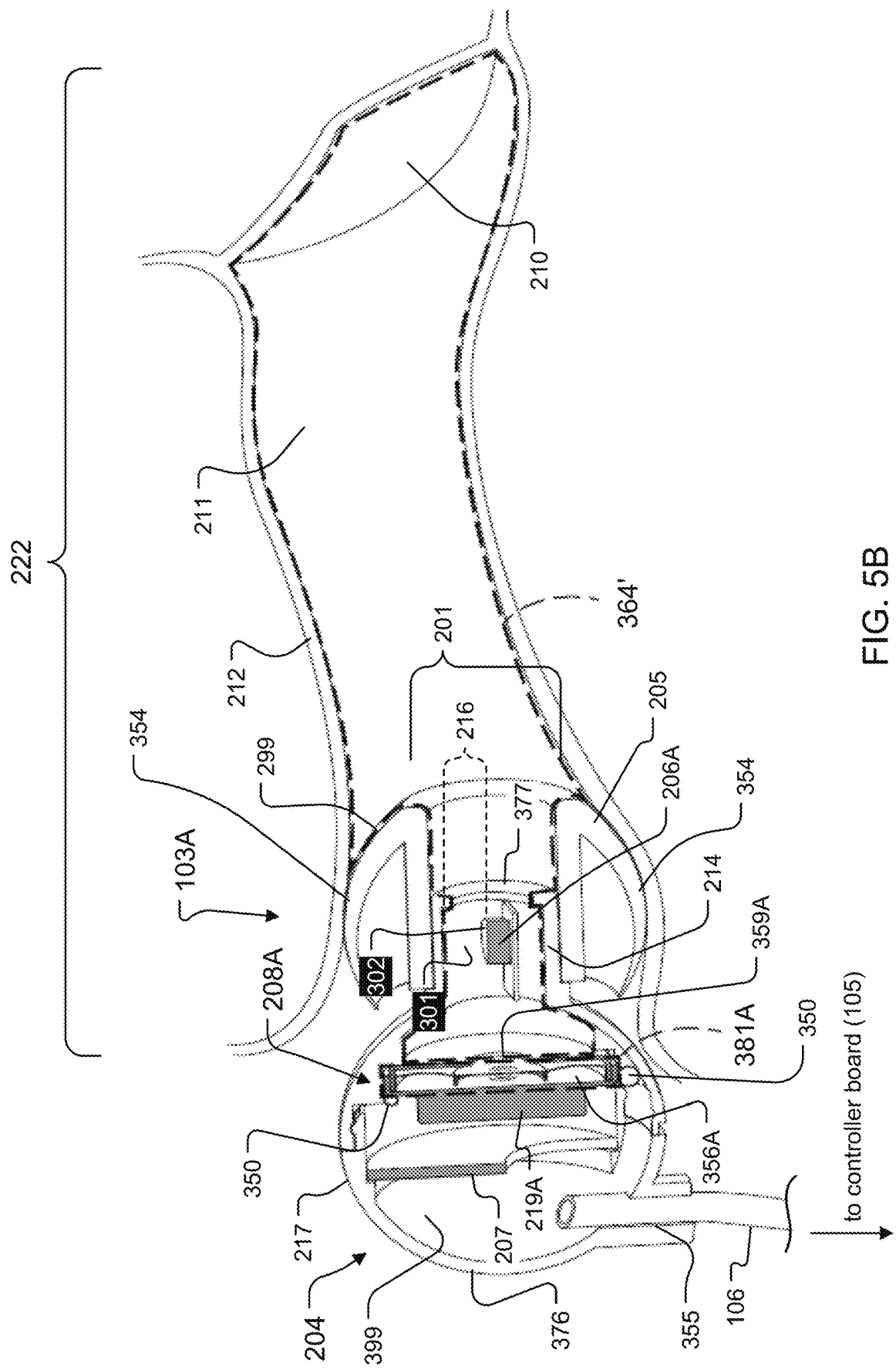

FIG. 5B provides more detail for the embodiment of the earbud 103A in FIG. 5A.

As expressed hereinabove, reducing the ear canal acoustic volume 384 will increase the acoustic pressure caused by the biosignals 101. Conversely, adding volume to the ear canal acoustic volume 384 will reduce the acoustic pressure of the biosignals 101.

In the illustrated example, an effective acoustic volume 381A of speaker 208A and an inner ear canal acoustic volume 364' are shown. Here, the inner ear canal acoustic volume 364' is formed from a combination of the inner ear canal and a cavity within the nozzle 214 that is now opened to the inner ear canal 211. This cavity extends from the earbud opening 201 and into the nozzle 214, up until the diaphragm 356A of the speaker 208A.

The earbud 103A must be designed such that its overall acoustic volume is comparable to that of the ear canal volume, or less, so that the reduction of the bioignal acoustic pressure (due to the presence of the speaker 208A) will be less than some tolerable amount. In this example, the speaker 208A refers to an acoustical subsystem that includes the physical sound transducer component embodied by the speaker, and any back-acoustical loads that may be present around the transducer. These back-acoustical loads can include air constrained (trapped) behind the transducer, any ports connected between the trapped air behind the transducer, and any air in front of the transducer.

As a result, the speaker 208A must have an effective acoustic volume 381A that is on the order of or less than than of the inner ear canal acoustic volume 364'. Stated another way, the stiff speaker 208A is part of an acoustical subsystem that includes the speaker 208A and any back-acoustical loads that may be present around the speaker 208A. This acoustical subsystem has an effective acoustic volume 381A that is less than than the inner ear canal acoustic volume 364'. More precisely, the stiffness of the speaker 208A must be equal to or greater than the stiffness of the inner ear canal 211.

Figure 6:
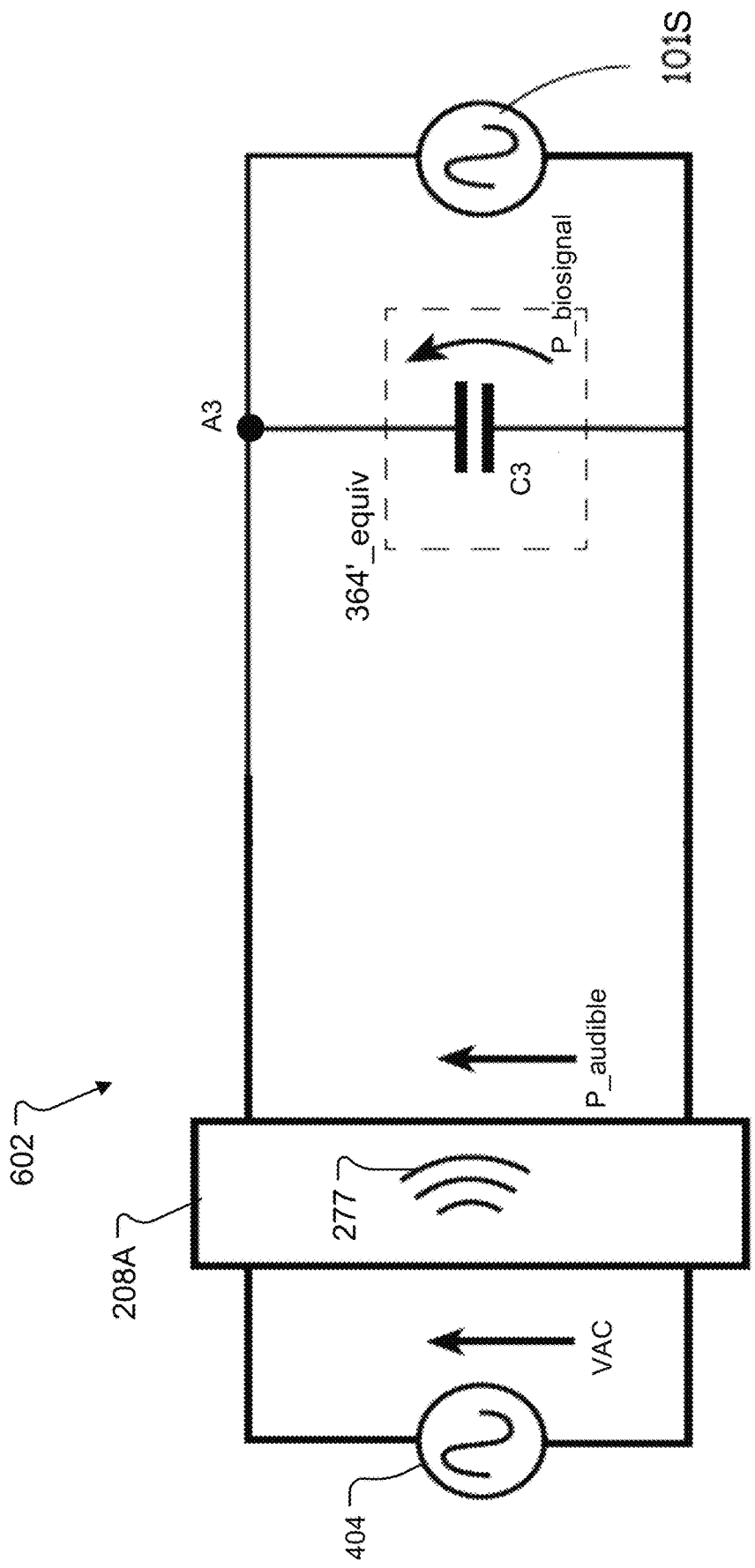
FIG. 6 is an equivalent electrical circuit for the mechano-acoustical system of FIG. 5B.

FIG. 6 is an equivalent electrical circuit 602 for the mechano-acoustical system of the earbud 103A described in FIG. 5B. The electrical circuit 602 models behavior of and components within the mechano-acoustical system using principles of duality.

The circuit 602 includes various circuit components that "map" to corresponding components and acoustical volumes in FIG. 5B. These circuit components include an alternating current source 404, the speaker 208A, capacitor C3, and biosignal source 101S. One parallel circuit branch indicated by reference A3 is also shown.

The mechano-acoustical system of the earbud 103 maps to the circuit 602 as follows. The voltage from the audio source is modeled as the alternating voltage source 404. The direction of the voltage is indicated by VAC. The acoustic pressure of the audio signals, created by the speaker 208A, and its direction, is indicated by reference P_audible. The speaker effective acoustic volume 381A is incorporated within the speaker model 208A. The physiological sources of biological signals is modeled as 101S and the pressure that the biosignals 101 add to the inner ear canal volume 364' is indicated as P_biosignal.

The inner ear canal acoustic volume 364' is modeled as parallel branch A3 and is indicated by reference "364' equiv." The circuit branch A3 includes capacitor C3.

Figure 7:
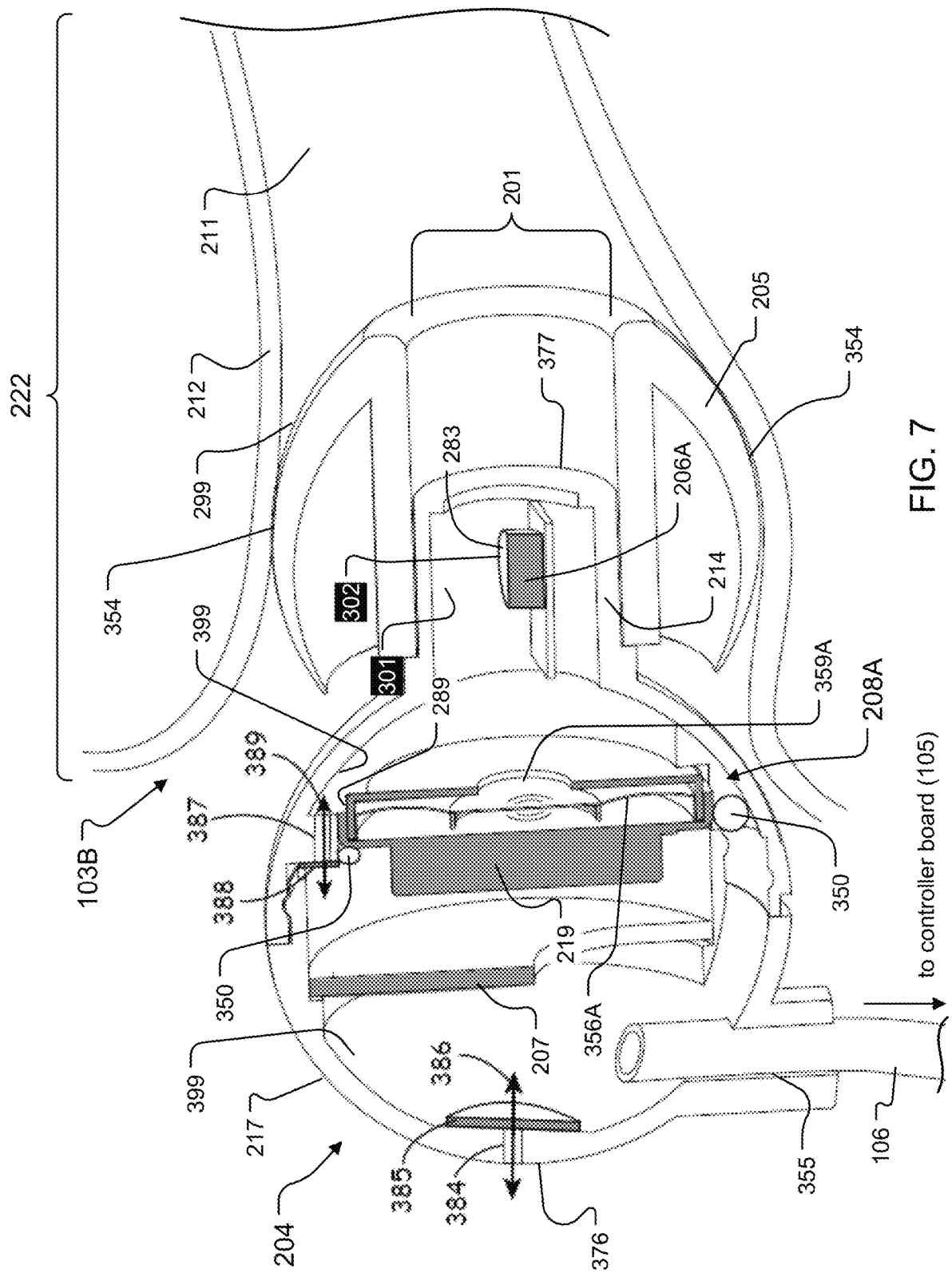
FIG. 7 is a cutaway view of an earbud, according to still another embodiment, as deployed in a cross-sectional anatomical depiction of an individual's ear.

FIG. 7 shows yet another embodiment of an earbud, earbud 103B.

The earbud includes a distal opening/port 384 in housing body 217 at distal end 376, a distal filter 385, a controlled opening 387 at the top of the speaker 208A, and a controlled opening filter 388.

The distal opening/port 384 enables outside air flow 386 into the housing body 217. The distal filter 385 is placed over the distal opening 384, and may be attached to inside wall 399 of the housing body or included within the distal opening 384. The distal filter 385 and distal port/opening 384 can be used to tune the transmitted audio signals 277.

The controlled opening 387 is located between a top surface of speaker 208A and the inside wall 399 of the housing body 217. The controlled opening 387 allows air flow 389 between the housing body 217 and the nozzle 214. The controlled opening filter 388 is either placed in front of the controlled opening 387 at the back portion 219 of the speaker 208A, or included within the controlled opening 387. As with the port 216 in the earbud 103 of FIG. 3A-3D, the controlled opening filter 388 can be used to provide an impedance to restrict/attenuate the biosignals 101 that might otherwise enter the housing body 217 via the controlled opening 387.

Figure 8:
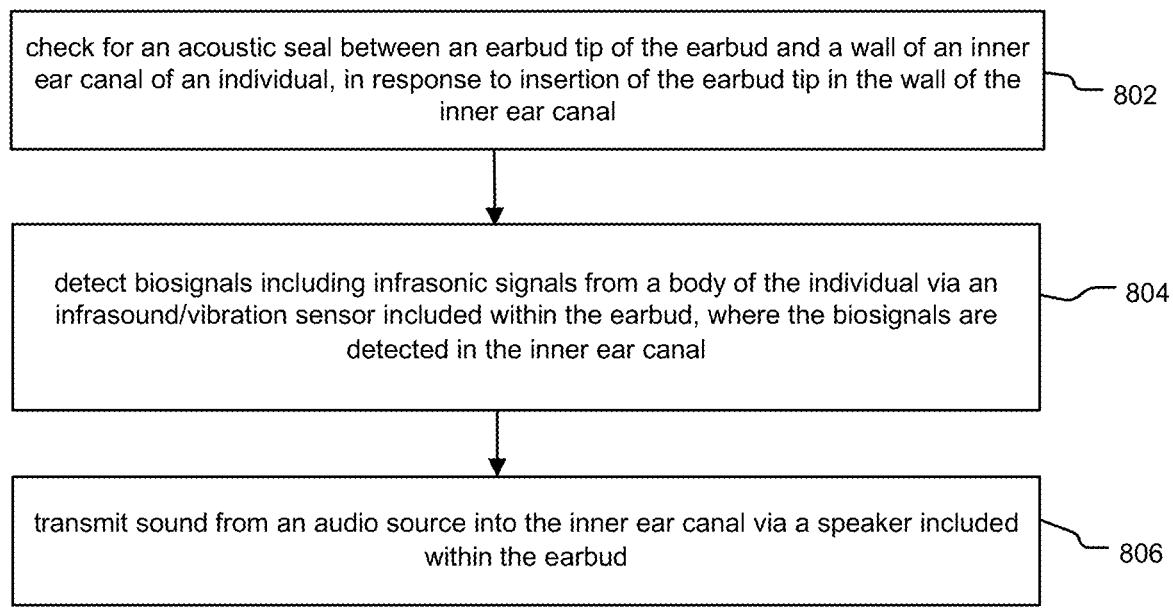
FIG. 8 is a flow chart that describes a method of operation of the earbuds in the embodiments referenced herein above.

FIG. 8 is a flow chart that describes a method of operation of the earbuds 103/103A/103B.

In step 802, an earbud including an earbud tip 205 checks for an acoustic seal 354 between the earbud tip 205 and the wall 212 of an inner ear canal 211 of an individual 100, in response to insertion of the earbud tip 205 in the wall 212 of the inner ear canal 212. In one implementation, the pressure sensor can monitor the acoustic seal 354 or provide static pressure as a baseline for the biosignals detected by the infrasound/vibration sensor 206. The earbud could then determine whether the pressure is equal to or greater than a threshold amount.

Alternatively, the acoustic seal 354 could be monitored using the acoustic/vibration sensor. In this example, the level of the seal 354 is related to and can be inferred from a magnitude of the infrasonic signals of the biosignals 101. The earbud could then determine whether a magnitude of the infrasonic signals is equal to or greater than a threshold amount.

According to step 804, the earbud detect biosignals 101 including infrasonic signals from the body of the individual 100, via an infrasound/vibration sensor included within the earbud. The biosignals 101 are detected in the inner ear canal 211.

In step 806, the earbud also transmits audio sound 277 from an audio source into the inner ear canal 211 via a speaker included within the earbud.

While this invention has been particularly shown and described with references to preferred embodiments thereof, it will be understood by those skilled in the art that various changes in form and details may be made therein without departing from the scope of the invention encompassed by the appended claims.

What is claimed is:

1. An earbud, comprising:
   a nozzle and a housing including a body, wherein the nozzle extends from the housing body and has a proximal end arranged for positioning within an inner ear canal of an individual;
   an earbud tip attached to the proximal end of the nozzle that is adapted to engage the inner ear canal, wherein the earbud tip suspends the nozzle within the inner ear canal when engaged; and
   a speaker and an infrasonic/vibration sensor, wherein the sensor detects biosignals including infrasonic signals from a body of the individual in the inner ear canal, and wherein the speaker reproduces sound from an audio source and transmits the sound into the inner ear canal via the nozzle.

2. The earbud of claim 1, wherein a face of the earbud tip forms an acoustic seal with a wall of the inner ear canal when the earbud tip is engaged, to acoustically isolate the inner ear canal from sounds external to the body of the individual.

3. The earbud of claim 2, wherein the earbud includes a pressure sensor located within the nozzle that the earbud uses to monitor the acoustic seal.

4. The earbud of claim 2, wherein the earbud uses the infrasound/vibration sensor to monitor the acoustic seal.

5. The earbud of claim 2, wherein the acoustic seal increases body-generated acoustical pressure within the inner ear canal, which increases an amplitude of the biosignals in the inner ear canal.

6. The earbud of claim 1, wherein the infrasonic/vibration sensor is included in the nozzle near the proximal end.

7. The earbud of claim 1, wherein the nozzle includes a port located between a top surface of the infrasound/vibration sensor and an inside wall of the nozzle, wherein the transmitted sound from the speaker propagates through the nozzle and into the inner ear canal via the port.

8. The earbud of claim 7, wherein the port has an acoustic impedance that effectively prevents the biosignals from entering the nozzle.

9. The earbud of claim 7, wherein the speaker is an acoustically compliant speaker that has an effective acoustic volume that is equal to or greater than an acoustic volume of the inner ear canal.

10. The earbud of claim 1, wherein the speaker is included in the housing body, and wherein the speaker forms an acoustic seal with an inside wall of the housing body to prevent air and the biosignals from entering the housing body.

11. The earbud of claim 1, wherein the speaker includes a sealed back portion that prevents air flow from the housing body into the speaker.

12. The earbud of claim 1, wherein the speaker is an acoustically stiff speaker that has an effective acoustic volume that is on the order of or less than an acoustic volume of the inner ear canal.

13. The earbud of claim 1, wherein the housing body includes a controlled port located between a top surface of the speaker and an inside wall of the housing body that enables air flow between the housing body and the nozzle.

14. The earbud of claim 13, wherein the housing body further includes a controlled opening filter placed in front of or within the controlled port, and wherein the filter is configured to provide an impedance that prevents the biosignals from entering the housing body via the controlled port.

15. The earbud of claim 1, wherein the housing body includes a distal port located at the distal end of the housing body, and wherein the distal port enables outside air flow into and out of the housing body.

16. The earbud of claim 15, wherein the housing body further includes a distal filter placed over or within the distal port, and wherein the distal filter is configured to provide an acoustic impedance that tunes the transmitted audio signals.

17. A method of operation of an earbud, the method comprising:

checking for an acoustic seal between an earbud tip of the earbud and a wall of an inner ear canal of an individual, in response to insertion of the earbud tip in the wall of the inner ear canal;

detecting biosignals including infrasonic signals from a body of the individual in the inner ear canal of the individual, via an infrasound/vibration sensor included within the earbud; and transmitting sound from an audio source into the inner ear canal via a speaker included within the earbud.

18. The method of claim 17, wherein checking for an acoustic seal between an earbud tip of the earbud and a wall of an inner ear canal of an individual comprises a pressure sensor included within the earbud sensing a pressure in the inner ear canal, and the earbud determining whether the pressure is equal to or greater than a threshold amount.

19. The method of claim 17, wherein checking for an acoustic seal between an earbud tip of the earbud and a wall of an inner ear canal of an individual comprises the infrasound/vibration sensor detecting the infrasonic signals of the biosignals, and the earbud determining whether a magnitude of the infrasonic signals is equal to or greater than a threshold amount.

20. The method of claim 17, further comprising the acoustic seal increasing body-generated acoustical pressure within the inner ear canal, which increases an amplitude of the biosignals in the inner ear canal.

\* \* \* \* \*